United States Patent
Wu et al.

[11] Patent Number: 5,994,587
[45] Date of Patent: Nov. 30, 1999

[54] PROCESS FOR PURIFYING NEOMENTHYLDIPHENYLPHOSPHINE USING METHANOL

[75] Inventors: Tse-Chong Wu; K. Pushpananda A. Senaratne, both of Baton Rouge, La.

[73] Assignee: Albemarle Corporation, Richmond, Va.

[21] Appl. No.: 09/084,623

[22] Filed: May 26, 1998

Related U.S. Application Data

[63] Continuation-in-part of application No. 08/797,067, Feb. 10, 1997, abandoned.

[51] Int. Cl.$^6$ .................................................. C07F 09/50
[52] U.S. Cl. ............................................... 568/17; 568/8
[58] Field of Search ............................................ 568/17, 8

[56] References Cited

U.S. PATENT DOCUMENTS

| | | | |
|---|---|---|---|
| 5,354,894 | 10/1994 | Devon | 568/17 |
| 5,654,486 | 8/1997 | Senaratne | 568/17 |
| 5,710,340 | 1/1998 | Senaratne | 568/17 |
| 5,777,169 | 6/1998 | Layman, Jr. | 568/17 |
| 5,866,720 | 2/1999 | Layman, Jr. | 568/17 |

FOREIGN PATENT DOCUMENTS

| | | |
|---|---|---|
| 1066261 | 4/1967 | United Kingdom . |
| 1295746 | 11/1972 | United Kingdom . |
| 2097795 | 11/1982 | United Kingdom . |
| 9741131 | 11/1997 | WIPO . |

OTHER PUBLICATIONS

Tanaka et al., "A Novel Route to Menthyldiphenylphosphine", Bull. Of the Chem. Soc. of Japan, vol. 48(3), 1975, p. 1094.

Aguiar et al., "Lithium Diphenylphosphide: A Convenient Source and Some Reactions, Journal of Organic Chemistry", vol. 27, 1962, pp. 1001–1005.

Hayashi et al., "Catalytic Asymmetric Hydroformylation by the Use of Rhodium–complexes of Chiral Bidentate Phosphorus Ligands Bearing Saturated Ring Skeletons", Bull. of the Chem. Soc. of Japan, vol. 52(9), 1979, pp. 2605–2608.

Morrison et al., "Synthesis of Menthyl–and Neomenthyldiphenylphosphine. Epimeric, Chiral, Tertiary Phosphine Ligands for Asymmetric Synthesis", J. Org. Chem., vol. 39(2), 1974, pp. 270–272.

Aguiar et al., "Stereochemistry of Diphenylphosphide Displacement at Saturated Carbon. Conformation and Relative Reactivity of Menthyl–and Neomenthyldiphenylphosphine Homogeneous Hydrogenation Complexes", J. Org. Chem., vol. 41(9), 1976, pp. 1545–1547.

*Primary Examiner*—Paul J. Killos
*Assistant Examiner*—Jean F Vollano
*Attorney, Agent, or Firm*—Philip M. Pippenger

[57] ABSTRACT

A process for the purification of crude neomenthyldiphenylphosphine, the process comprising crystallizing the crude neomenthyldiphenylphosphine using a solvent consisting essentially of methanol. The process provides for the unexpectedly efficient production of neomenthyldiphenylphosphine having purities of at least 97 mole percent, and more preferably at least about 99 mole percent. Another embodiment of the invention is neomenthyldiphenylphosphine having a purity of at least 97 mole percent produced by crystallizing crude neomenthyldiphenylphosphine having a purity of less than 97 mole percent using a solvent consisting essentially of methanol.

15 Claims, No Drawings

PROCESS FOR PURIFYING NEOMENTHYLDIPHENYLPHOSPHINE USING METHANOL

REFERENCE TO RELATED APPLICATION

This is a continuation-in-part of co-pending U.S. patent application Ser. No. 08/797,067 filed Feb. 10, 1997.

TECHNICAL FIELD

This invention relates to recrystallization processes for purifying neomenthyldiphenylphosphine.

BACKGROUND

Methods for the production of air-sensitive phosphines such as, for example, trihydrocarbylphosphines having at least one aryl group and at least one alkyl or cycloalkyl group in the molecule, have been reported in the literature. Prior methods for the purification of reaction products containing desired forms of these phosphines have involved recrystallization in which ethanol was used as a solvent. However, these previous methods result in purity levels of no greater than 95% as measured by gas chromatography, purity levels which have proven to be inadequate in commercial applications of trihydrocarbylphosphines which are important catalyst components such as, e.g., neomenthyldiphenylphosphine.

Thus, a need exists for a way to produce highly pure (at least 97 mole percent as measured by $^{31}$P NMR analysis) neomenthyldiphenylphosphine. This invention is deemed to fulfill this important need in a surprisingly efficient and effective manner.

DESCRIPTION OF THE INVENTION

In one embodiment, this invention provides a new, surprisingly effective process for producing highly pure neomenthyldiphenylphosphine. More particularly, this invention provides a process for the purification of neomenthyldiphenylphosphine from crude neomenthyldiphenylphosphine under an inert atmosphere the process comprising crystallizing the crude neomenthyldiphenylphosphine using a solvent consisting essentially of methanol. Preferably, the purity of the crystallized neomenthyldiphenylphosphine is at least 97 mole percent, and more preferably at least about 99 mole percent, measured by $^{31}$P NMR analysis. This process reveals that methanol achieves unexpectedly superior results as a crystallization solvent for neomenthyldiphenylphosphine as compared to results achieved when ethanol is employed as a solvent in the crystallization process.

Another embodiment of this invention is neomenthyldiphenylphosphine (also referred to herein as NMDPP) having a purity of at least 97 mole percent as measured by $^{31}$P NMR analysis produced by crystallizing crude neomenthyldiphenylphosphine having a purity of less than 97 mole percent as measured by $^{31}$P NMR analysis using a solvent consisting essentially of methanol. NMDPP of this invention has a solubility in methanol of less than 2.0% by weight at 25° C. and of less than 9.0% by weight at 60° C. In a preferred embodiment, the NMDPP has a purity of at least 99 mole percent measured by $^{31}$P NMR analysis produced by crystallizing crude NMDPP having a purity of less than 99 mole percent measured by $^{31}$P analysis using a solvent consisting essentially of methanol.

The purification process of this invention has been found capable of producing highly pure product even when starting with a crude mixture comprised of neomenthyldiphenylphosphine and from about 2 to about 60 mole percent of one or more impurities including oxide derivatives of neomenthyldiphenylphosphine.

The step of crystallization in this invention is conducted using preferably degassed solvent in which the crude neomenthyldiphenylphosphine is dissolved. The purified product is removed from the resulting solution as a crystalline precipitate by heating the solution to a temperature in the range of about 40 to about 65° C., slowly (i.e., for a period of at least about 2 hours) cooling the solution to form the crystalline precipitate, and then removing the precipitate by filtration. In this way, the impurities substantially remain in solution so that the resulting crystalline precipitate is highly pure. Recrystallization may be employed to achieve even higher levels of purity, if desired. In such cases, the crystallization step is repeated by using the crystalline precipitate of each previous crystallization as the starting material for a subsequent crystallization until the desired level of purity is attained.

The solvent used consists essentially of methanol, but may include small amounts of impurities such as, for example, water and ethanol, so long as the impurities do not negatively affect the level of product purity attained in the process. The amount of solvent used is typically in the range of about 1 to about 50 mL of solvent per gram of the crude neomenthyldiphenylphosphine, although other amounts of solvent may be used, if desired, to optimize the yield of purified NMDPP.

The following comparative examples serve to illustrate this invention, but do not limit it.

EXAMPLE 1

Comparative

Diphenylphosphine (140 g, 0.75 mol) was charged into a 2-L, 3-neck, round-bottom flask in a glove box under a nitrogen atmosphere. The reactor was connected to a nitrogen manifold. Freshly distilled tetrahydrofuran (400 mL) was added to the mixture and the mixture was cooled to −20° C. Normal butyllithium (1.6 M in hexanes, 468 mL, 0.75 mol) was added over a 2 hour period. The cold bath was removed and the orange solution was warmed to room temperature. After stirring at room temperature for 0.5 hour, (−)-menthyl chloride (129 g, 0.74 mol) was added. The mixture was stirred at room temperature for 21 hours and then heated at reflux for 40 hours. The reaction mixture was cooled to room temperature and quenched with H$_2$O (125 mL). After stirring for 2 hours, the organic layer was separated, washed with H$_2$O (125 mL) and concentrated to an oil. The resulting material was distilled under vacuum until crystal formation was observed in the distillation condenser to give about 130 g of crude NMDPP in the pot.

Crystallization of the crude NMDPP from ethanol (700 mL) gave a white solid (75 g). Analysis by $^{31}$P NMR showed 83 mole percent NMDPP, 10 mole percent NMDPP oxide, and 3 mole percent diphenylphosphine oxide. The mother liquor was cooled to minus 40° C. and yielded another 23 g of product. Analysis by $^{31}$P NMR showed 77 mole percent NMDPP, 14 mole percent NMDPP oxide, and 4 mole percent diphenylphosphine oxide. In this and each of the examples which follow, the $^{31}$P NMR analysis was conducted using a General Electric QE300 NMR machine set at 121.7 MHZ, each sample having been prepared under nitrogen in a glove box.

EXAMPLE 2

Comparative

NMDPP (85%, 1 g) was chromatographed on silica gel (230–400 mesh, 30 g, eluted with a degassed 20:1 hexanes/

EtOAc solvent) in a nitrogen glove box. The solvent was removed under vacuum to give a white solid. Analysis by $^{31}$P NMR showed 92 mole percent NMDPP and 7 mole percent NMDPP oxide.

EXAMPLE 3

Recrystallization of NMDPP (3 gms of 83% pure NMDPP from Example 1) from methanol (degassed, 60 mL) under a nitrogen atmosphere gave a crystalline solid (1.8 g). Analysis by $^{31}$P NMR showed greater than 99 mole percent NMDPP.

EXAMPLE 4

In a 2-L, three-necked round-bottom flask, diphenylphosphine (164.9 gms, 0.885 mols) was dissolved in degassed THF (500 mL) and cooled to minus 20° C. in a nitrogen glove box. The reactor was connected to a nitrogen manifold. A solution of normal butyllithium in pentane (0.885 mol) was added dropwise to the solution. The cold bath was removed, and the orange colored solution was warmed to room temperature. The solution then was added to a solution of menthyl chloride (0.885 mol) in degassed THF (100 mL) at 60° C. The reaction was refluxed for 60 hours and then cooled. Degassed water (200 mL) was then added and the solution was stirred for 30 minutes. The organic phase was separated and concentrated to a thick oil. The oil was distilled under vacuum until crystal formation was observed in the distillation condenser. The residue was recrystallized by being dissolved in degassed methanol. Upon cooling, NMDPP was precipitated as a white solid. The purity of the precipitate was measured by gas chromatography to be greater than 96 area %.

EXAMPLE 5

A solution of menthyl mesylate (22.2 g, 0.095 mol) in tetrahydrofuran (50 mL) was placed in a flame-dried, 3-neck flask fitted with a dropping funnel, condenser, and an overhead stirrer. An equivalent amount of sodium diphenylphosphide in tetrahydrofuran was added and the mixture was heated to reflux for 30 minutes. The mixture was cooled to room temperature and 100 mL of degassed, distilled water was added. After stirring for 20 minutes, the organic layer was separated and stripped to remove the solvent. The resulting crude solid was dissolved in degassed methanol (50 mL) at reflux and cooled to 0° C. to precipitate NMDPP as beige crystals. The yield was 80% and the purity by $^3$P NMR analysis was greater than 95 mole percent.

In Examples 6 and 7, the solubility of crude NMDPP in methanol was compared to the solubility of purified NMDPP in methanol by determining the temperatures at which various weight percents of crude NMDPP and purified NMDPP, respectively, fail to completely dissolve in solution based upon visual inspection, i.e., when the otherwise clear solution began to become cloudy in appearance.

EXAMPLE 6

Solubility was determined for crude NMDPP made in accordance with Example 4 (prior to recrystallization) in methanol which was degassed with nitrogen for 2 hours. The solubility tests were carried out under nitrogen in a glove box and the results are set forth in Table 1 below.

TABLE 1

| Temperature, ° C. | Weight Percent |
| --- | --- |
| 40.5 | 9.99 |
| 47.8 | 18.35 |
| 50 | 27.74 |
| 56.8 | 49.76 |
| 55.8 | 59.48 |

EXAMPLE 7

Solubility of NMDPP purified through crystallization in methanol degassed with nitrogen for 2 hours was measured. The solubility tests were carried out under nitrogen in a glove box and the results are set forth in Table 2 below.

TABLE 2

| Temperature, ° C. | Weight Percent |
| --- | --- |
| 8 | 1.00 |
| 25.5 | 1.80 |
| 34.1 | 2.58 |
| 42 | 3.91 |
| 48.7 | 5.21 |
| 52.7 | 6.38 |
| 60.4 | 8.46 |

Examples 8–11 provide still further demonstrations of the excellent results achievable by the practice of this invention as compared to prior art usage of ethanol as the crystallization solvent.

EXAMPLE 8

Crude NMDPP (14.0 g) and MeOH (degassed, 40 g) were heated at 65° C. for 20 minutes. The clear solution was slowly cooled to 25° C. overnight. The solid was collected by filtration and washed with MeOH (2×8 g). The resultant solid was dried under vacuum to give a white solid (4.62 g). This example and the following Comparative Example 9 were carried out side-by-side in a nitrogen glove box.

EXAMPLE 9

Comparative

Crude NMDPP (14.0 g) and EtOH (degassed, 40 g) were heated at 65° C. for 20 minutes. The clear solution was slowly cooled to 25° C. overnight. The solid was collected by filtration and washed with EtOH (2×8 g). The resultant solid was dried under vacuum to give a white solid (3.25 g).

EXAMPLE 10

Crude NMDPP (14.0 g) and MeOH (degassed, 52 g) were heated at 65° C. for 20 minutes. The clear solution was slowly cooled to 25° C. over 5 hours and then kept at 0° C. overnight. The solid was collected by filtration and washed with MeOH (2×8 g). The resultant solid was dried under vacuum to give a white solid (5.13 g). This example and the following Comparative Example 11 were carried out side-by-side in a nitrogen glove box.

EXAMPLE 11

Comparative

Crude NMDPP (14.0 g) and EtOH (degassed, 52 g) were heated at 65° C. for 20 minutes. The clear solution was slowly cooled to 25° C. over 5 hours and then kept at 0° C. overnight. The solid was collected by filtration and washed with EtOH (2×8 g). The resultant solid was dried under vacuum to give a white solid (4.32 g).

A comparison of the results obtained in Examples 8 and 10 and Comparative Examples 9 and 11 are set forth below in Table 3.

TABLE 3

|  | Crude NMDPP | Example 8 | Example 9 (Comparative) | Example 10 | Example 11 (Comparative) |
|---|---|---|---|---|---|
| Yield, grams | — | 4.62 | 3.25 | 5.13 | 4.32 |
| Relative yield | — | 1.42 | 1 | 1.19 | 1 |
| Yield improvement, % | — | 42 | — | 19 | — |
| $^{31}$P NMR NMDPP purity, mol % | 46.1 | 98.9 | 98.4 | 98.7 | 98.1 |
| $^{31}$P NMR NMDPP oxide, mol% | 6.0 | 0.77 | 1.51 | 0.90 | 1.73 |
| Relative NMDPP oxide content | — | 1 | 1.96 | 1 | 1.92 |
| Relative oxide improvement, % | — | 51 | — | 52 | — |

As may be seen from the above examples and comparative examples, unexpected, surprisingly beneficial results are achieved when methanol is used as a solvent in the crystallization of the trihydrocarbylphosphine compound. This purity is exemplified by the substantially reduced solubility of the pure neomenthyldiphenylphosphine in methanol after crystallization as compared to the solubility of the crude neomenthyldiphenylphosphine compound, as well as the data set forth above in Table 3 showing yield, purity and oxide impurity improvements as compared with processes not of this invention.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the purification of crude neomenthyldiphenylphosphine, which process comprises crystallizing said crude neomenthyldiphenylphosphine under an inert atmosphere using a solvent consisting essentially of methanol.

2. A process according to claim 1 wherein the crude neomenthyldiphenylphosphine contains from about 2 to about 60 mole percent of one or more impurities including the oxide derivative of neomenthyldiphenylphosphine, and wherein the methanol is degassed methanol.

3. A process according to claim 2 wherein the crystallized neomenthyldiphenylphosphine has a purity of at least 97 mole percent as measured by $^{31}$P NMR.

4. A process according to claim 3 wherein the crystallized neomenthyldiphenylphosphine has a purity of at least 99 mole percent as measured by $^{31}$P NMR.

5. A process for the purification of crude neomenthyldiphenylphosphine containing from about 2 to about 60 mole percent of one or more impurities including the oxide derivative of neomenthyldiphenylphosphine, which process comprises (i) dissolving said crude neomenthyldiphenylphosphine in a degassed solvent consisting essentially of methanol, (ii) heating the resultant solution to a temperature in the range of about 40 to about 65° C., (iii) slowly cooling the solution to form a crystalline precipitate of purified neomenthyldiphenylphosphine, and (iv) recovering the purified neomenthyldiphenylphosphine.

6. A process according to claim 5 wherein the crystallized neomenthyldiphenylphosphine has a purity of at least 97 mole percent as measured by $^{31}$P NMR.

7. A process according to claim 6 wherein the crystallized neomenthyldiphenylphosphine has a purity of at least 99 mole percent as measured by $^{31}$P NMR.

8. A process according to claim 6 wherein the crude neomenthyldiphenylphosphine is produced by (a) reacting diphenylphosphine with n-butyllithium in tetrahydrofuran and then mixing (−)-menthyl chloride with the resultant reaction mixture such that the ensuing reaction forms a reaction mass comprising neomenthyldiphenylphosphine; (b) quenching the reaction mass with water to form a two-phase mixture; (c) separating and concentrating the organic phase to form oil; and (d) distilling the oil under vacuum to remove volatiles therefrom and to thereby form the crude neomenthyldiphenylphosphine as the distillation residue.

9. A process according to claim 8 wherein the tetrahydrofuran is freshly-distilled tetrahydrofuran.

10. A process according to claim 8 wherein the tetrahydrofuran is degassed tetrahydrofuran.

11. A process according to claim 10 wherein the water is degassed water.

12. A process according to claim 6 wherein the crude neomenthyldiphenylphosphine is produced by (a) reacting sodium diphenylphosphide with menthyl mesylate in tetrahydrofuran to form a reaction mass comprising neomenthyldiphenylphosphine; (b) quenching the reaction mass with water to form a two-phase mixture; and (c) separating and stripping the organic phase of said two-phase mixture to remove the solvent therefrom and to thereby form crude neomenthyldiphenylphosphine as the distillation residue.

13. A process according to claim 12 wherein the water is degassed, distilled water.

14. Neomenthyldiphenylphosphine having a purity of at least 97 mole percent produced by crystallizing crude neomenthyldiphenylphosphine having a purity of less than 97 mole percent using a solvent consisting essentially of methanol.

15. The compound of claim 14 having a purity of at least about 99 mole percent produced by crystallizing crude neomenthyldiphenylphosphine having a purity of less than about 99 mole percent.

* * * * *